US000001028H

United States Statutory Invention Registration [19]

[11] Reg. Number: H1028

Falk et al.

[43] Published: Mar. 3, 1992

[54] MEDICAL FORCEPS

[75] Inventors: Ernst Falk, Sternenfels-Diefenbach; Andreas Dingler, Birkenfeld; Siegfried Hiltebrandt, Knittlingen, all of Fed. Rep. of Germany

[73] Assignee: Richard Wolf GmbH, Knittlingen, Fed. Rep. of Germany

[21] Appl. No.: 679,650

[22] Filed: Apr. 2, 1991

[30] Foreign Application Priority Data

Apr. 4, 1990 [DE] Fed. Rep. of Germany ..... 4010775

[51] Int. Cl.[5] ..... A61B 17/28

[52] U.S. Cl. ..... 606/205

*Primary Examiner*—Michael J. Carone

*Attorney, Agent, or Firm*—Cohen, Pontani & Lieberman

[57] ABSTRACT

Medical forceps are described which have a fixed jaw part and swingable jaw part with which parts a fixed handle part and a swingable handle part respectively are associated. In order to limit the pressure force which can be produced on the jaw parts, the swingable grip part is divided into two parts which are undetachably connected on a line with each other by a flexural spring element. For the fixing of the gripping position of the jaw parts detent elements which come into detachable engagement with each other are provided on the grip parts.

3 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

MEDICAL FORCEPS

The present invention relates to medical forceps having a fixed jaw part with which a fixed grip part is associated and a movable jaw part which can be actuated by means of a swingable grip part which is coupled to the movable jaw part by a spring member which limits the actuating force.

Known forceps of this type are disclosed in Federal Republic of Germany Patent 30 01 166 in which a fixed jaw part and a swingable jaw part are associated with a fixed and swingable grip part respectively, the said last-mentioned grip part being divided into two individual parts which are articulated to each other and rest against each other via a spring member in order to limit the pressing force which can be produced on the jaw parts.

In this embodiment when a given pressure is exceeded although the lower part is disconnected from the other part which is then no longer swingable, upon further movements of the grip parts towards each other the old force of the jaw parts however increases further in correspondence with the characteristic curve of the spring member. The thus increasing force can lead to the perforating or even the cutting of the tissue present between the jaw parts.

The object of the present invention, therefore, is to improve the forceps in accordance with the above-described prior art in such a manner that a practically constant force can be exerted on the two jaw parts regardless of how far the two grip parts are moved towards each other.

This object is achieved in accordance with the invention in the manner that the swingable grip part consists of two parts which are on a line with each other and are undetachably connected to each other by a flexural spring member. In accordance with the preferred embodiment, the outer part of the swingable grip part as well as the rigid grip part can be provided in this connection with handles and be equipped, in known manner, with detent elements which correspond to each other.

Figure 1:
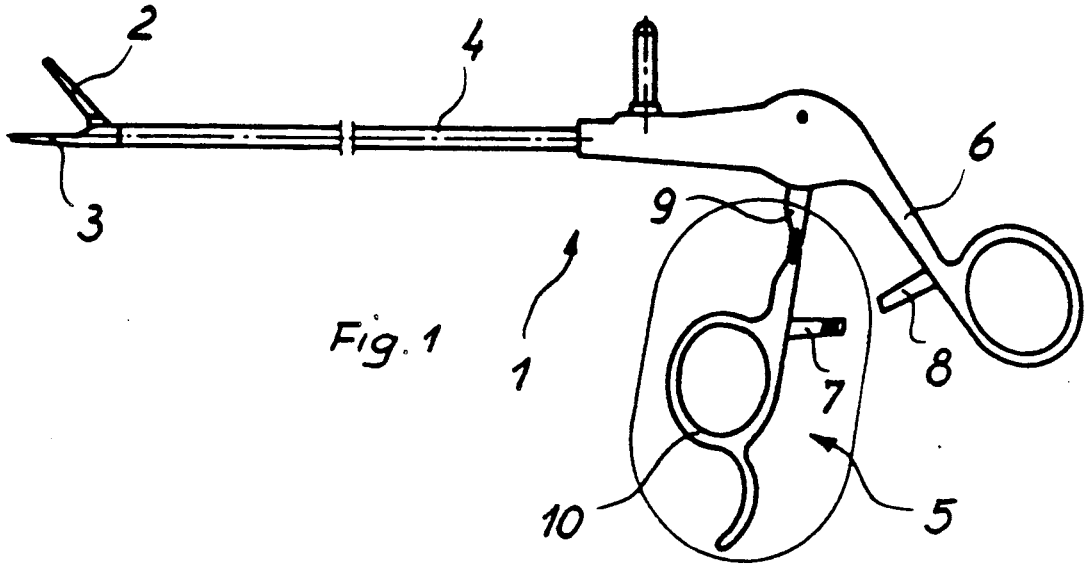
Figure 2:
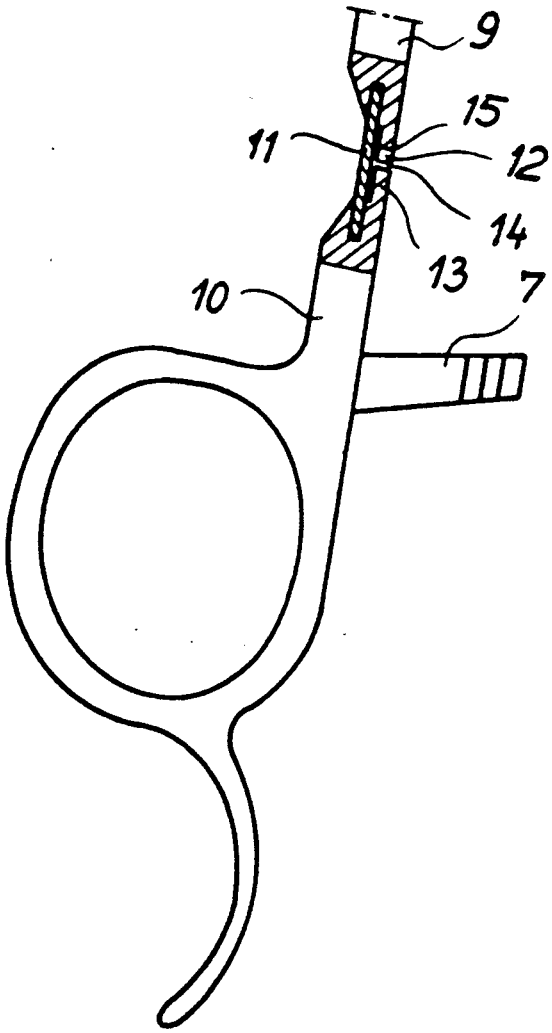

The forceps of the invention are described in further detail below with reference to an embodiment shown in the drawing, in which FIG. 1 is an overall side view of the forceps; FIG. 2 shows on a larger scale the part of the forceps of FIG. 1 which is developed in accordance with the invention.

FIG. 1 shows a forceps 1 having a rigid jaw part 3 and a swingable jaw part 2 which can be actuated via a pull and push rod (not shown) guided in the forceps shank 4 by means of a grip part 5 which is held against a rigid grip part 6. In order to be able to fix the two jaw parts 2 and 3 in the position holding the tissue fast, the two grip parts 5 and 6 have detent elements 7 which can be brought into detachable engagement with each other via a profiled surface.

The grip part 5 consists of an inner part 9 and an outer part 10, said parts being connected in undetachable manner to each other by means of a flat spring 11. The flat spring 11 is bridged over by support projections 12 and 13 except for a small space 14, a slight air space remaining between the support projections 12 and 13 and the flat spring 11.

If tissue not in excess of a given thickness is gripped by the two jaw parts 2 and 3, the space 14 between the two support projections 12 and 13 of the parts 9 and 10 respectively is, to be sure, reduced even if the detent elements 7 and 8 are engaged with each other, but the surfaces of the support projections 12 and 13 which define the space 14 do not come against each other. If the forceps are used in a manner not in accord with their purpose, i.e. if too much tissue or, for instance, cartilage is grasped by the two jaw parts 2 and 3, then the force required for the closing of said parts is so great that the two support projections 12 and 13 come against each other in the region of the space 14 and in this way form a safety stop which prevents permanent deformation of the spring element and which is transmitted on the outer part 9 directly to the swingable jaw part 2. In such case it can, of course, not be avoided that the disadvantages of the known prior art arise.

We claim:

1. Medical forceps having a fixed jaw part with which a fixed grip part is associated and a moveable jaw part which is actuatable by means of a swingable grip part, the latter being coupled with the moveable jaw part via a spring member which limits the actuating force, characterized by the fact that the swingable grip part (5) consists of two parts (9 and 10) which are in line with each other and are undetachably connected to each other by a flexural spring element (11).

2. Forceps according to claim 1, characterized by the fact that a safety stop which limits the deflection of the flexural spring element (11) is provided.

3. Forceps according to claim 1 or 2, characterized by the fact that the outer part (10) of the swingable grip part (5) as well as the grip part (6) fixed are provided with handles and equipped with detent elements (7 and 8) which correspond to each other.

* * * * *